United States Patent [19]
LaHann

[11] Patent Number: 5,935,944
[45] Date of Patent: *Aug. 10, 1999

[54] FORMULATION FOR I.V. ADMINISTRATION OF THE BORON DELIVERY DRUG, BORONOPHENYLALANINE (BPA)

[75] Inventor: Thomas R. LaHann, Pocatello, Id.

[73] Assignee: Neutron Technology Corporation, Boise, Id.

[ * ] Notice: This patent is subject to a terminal disclaimer.

[21] Appl. No.: 08/603,332

[22] Filed: Feb. 20, 1996

Related U.S. Application Data

[63] Continuation-in-part of application No. 08/119,982, Sep. 10, 1993, Pat. No. 5,492,900.

[51] Int. Cl.$^6$ .................................................. A61K 31/69
[52] U.S. Cl. .................................. 514/64; 514/23; 568/6; 536/124
[58] Field of Search .................................. 568/6; 514/23, 514/64; 536/124

[56] References Cited

U.S. PATENT DOCUMENTS

| | | | |
|---|---|---|---|
| 4,824,659 | 4/1989 | Hawthorne | 424/1.1 |
| 5,021,572 | 6/1991 | Gabel | 544/229 |
| 5,116,980 | 5/1992 | Gabel | 544/229 |
| 5,144,026 | 9/1992 | Gabel | 540/500 |
| 5,149,801 | 9/1992 | Kahl et al. | 540/145 |
| 5,157,149 | 10/1992 | Samsel | 562/7 |
| 5,492,900 | 2/1996 | LaHann | 514/64 |

FOREIGN PATENT DOCUMENTS 122720  9/1980  Japan .

OTHER PUBLICATIONS

LaHann, LR et al., Advances in Neutron Capture Therapy, Barth and Soloway, eds. 1 pp. 585–589, presented Sep. 14–17, 1992, Fifth International Symposium on Neutron Capture Therapy, Columbus, Ohio.

LaHann, Sills, et al., Advances in Neutron Capture Therapy, Barth and Soloway, eds; pp. 513–517, presented Sep. 14–17, 1992, Fifth International Symposium on Neutron Capture Therapy, Columbus, Ohio.

Barth, et al., Boron Neutron Capture Therapy for Cancer, Dec. 15, 1992, vol. 70, No. 12, pp. 2995–3007.

Soloway, et al., Evaluation of Boron Compounds for use in Neutron Capture Therapy of Brain Tumors. I. Animal Investigations, Mar. 10, 1961, vol. 134, pp. 117–122. J. Pharmacol. Exp. Therapeutics.

Mori, et al., Complex Formation of p–Boronophenylalanine With Some Monosaccharides, 1989, pp. 273–277 months not available.

Yoshino, et al., Improvement of solubility of p–boronphenylalanine by complex formation wtih monosaccharides, 1989, pp. 127–129 months not available.

Coderre, et al., Selective Targeting of Boronophenylalanine to Melanoma in BALB/c Mice for Neutron Capture Therapy, Sep. 10, 1987, pp. 6377–6383.

Coderre, et al., Selective Delivery of Boron by the Melanin Precursor Analog p–Boronophenylalanine to Tumors Others Than Melanoma, Oct. 2, 1989, pp. 138–141.

Mishima, et al., New Thermal Neutron Capture Therapy for Malignant Melanoma: Melanogenesis–Seeking $^{10}$B Molecule–Melanoma Cell Interaction From In Vitro to First Clinical Trial, Sep. 21, 1988, pp. 226–234.

Mallesch, et al., The Biodistribution of p–Boronophenylalanine–Fructose in Human Patients with Glioma and Metastatic Melanoma, 1993, pp. 735–738 months not available.

Buccholz, MD, et al., Concomitant Boron–Neutron Capture Therapy during Fast–Neutron Irradiation of a Rat Glioma[1], 1994, pp. 863–867 months not available.

Barth, et al., A Nude Rat Model for Neutron Capture Therapy of Human Intracerebral Melanoma, Int. J. Radiation Oncology Biol. Phys., vol. 28, No. 5, pp. 1079–1088, 1994 months not available.

Mallesch, et al., The Pharmacokinetics of P–Boronophenylalanine.Fructorse in Human Patients with Glioma and Metastatic Melanoma, Int. J. Radiation Oncology Biol, Phys., vol. 28, No. 5, pp. 1183–1188, 1994 months not available.

Matalka, et al., Radiation Effects of Boron Neutron Capture Therapy on Brain, Skin, and Eye of Rats, Int. J. Radiation Oncology Biol. Phys., vol. 28, No. 5, pp. 1089–1097, 1994 months not available.

Coderre, et al., Neutron Capture Therapy of the 9L Rat Cliosarcoma Using the P–Boronophenylalanine–Fructose Complex, Int. J. Radiation Oncology Biol. Phys., vol. 30, No. 3, pp. 643–652, 1994 months not available.

Setiawan, et al., Effect of L–$^{10}$B–p–Boronophenylalanine–fructose and the Boron Neutron Capture Reaction on Mouse Brain Dopaminergic Neurons[1], Feb. 15, 1995, pp. 874–877.

Fukuda, et al., Boron Neutron Capture Therapy of Malignant Melanoma Using $^{10}$B–Paraboronophenylalanine with Special Reverence to Evaluation of Radiation Dose and Damage to the Normal Skin, Radiation Research 138. 1994, pp. 435–442 months not available.

Matalka, Neutron Capture Therapy of a Rat Glioma Using Boronophenylalanine as a Capture Agent[1,2], Radiation Research 137, 1994, pp. 44–51 months not available.

*Primary Examiner*—Kathleen K. Fonda
*Attorney, Agent, or Firm*—Ken J. Pedersen; Barbara S. Pedersen

[57] ABSTRACT

A process and product formulated by complexing boronophenylalanine (BPA) and related compounds with a saccharide in an aqueous solution are disclosed. Formation of the complex is facilitated by raising the pH of the solution to a higher pH of about 10 or by lowering the pH of the solution to a lower pH of about 2 and then readjusting the pH to a body physiological pH of about 7.4. This BPA saccharide complex can then be delivered by i.v. or other injection or administered orally as a key component of the BNCT cancer treatment process The pH manipulation causes a much higher solubility of BPA or related compounds and thus a higher boron concentration in the tumor, thereby improving the therapy.

19 Claims, 1 Drawing Sheet

FORMULATION FOR I.V. ADMINISTRATION OF THE BORON DELIVERY DRUG, BORONOPHENYLALANINE (BPA)

DESCRIPTION

This application is a continuation in part application of, and claims priority from, U.S. patent application Ser. No. 08/119,982, filed on Sep. 10, 1993, which issued as U.S. Pat. No. 5,492,900 on Feb. 20, 1996, the disclosure of which is incorporated herein by this reference.

BACKGROUND OF THE INVENTION

1. Field of the Invention

A new method of drug formulation delivers more boron to malignant tumors and facilitates boron neutron capture therapy (BNCT) of cancers such as glioblastoma and malignant melanoma. Data indicate that the formulation method may improve BPA-mediated BNCT of cancer by a factor of as much as between 10 and 100 million and also offers a selectivity factor (i.e., ratio of the sensitivity of cancerous tissue to the sensitivity of normal tissue) of between 10 and 100 million.

2. Background of The Invention.

Boron neutron capture therapy (BNCT) is being developed as a treatment for cancer, including brain cancer and malignant melanoma. P-boronophenylalanine (BPA) was initially proposed as a boron (B) delivery drug for BNCT of malignant melanoma because it was postulated that this B-containing amino acid, by mimicking a melanin precursor, would selectively accumulate in melanoma cells. BPA does seem to selectively accumulate in cancer cells, apparently as a result of uptake by an amino acid transport system. For successful BNCT, tumor B concentrations of at least 20 ppm are thought to be necessary, but higher tumor B levels are desirable. Calculations indicate that for a given neutron exposure, doubling of the tumor B concentration can increase tumor cell kill by a factor of about 10,000 or more. Thus, even modest increases in the amount of B in tumor cells can dramatically improve the effectiveness of BNCT as a cancer treatment.

If amino acid transport systems accumulate BPA, then high extracellular concentrations of BPA should increase the amount of BPA entering cancer cells. I.V. infusion of BPA is the simplest route for delivering BPA to the tumor cells but is not widely used because at physiological pH (7.4), BPA exhibits poor water solubility (<4 ppm). One option for increasing BPA solubility is the use of organic complexes. Boric acid is known to complex with monosaccharides. Monosaccharides also increase BPA's aqueous solubility. However, BPA exists in different forms at different pH values and complexing of BPA with monosaccharides is a pH dependent process. I.V. administration of BPA-monosaccharide complexes created by pH manipulation increases the delivery of B to tumor tissue.

SUMMARY OF THE INVENTION

Generally stated, the invention is a process for formulating a d-,l- or l,d-boronophenylalanine solution for use in a BNCT cancer treatment, the process comprising:

mixing a molar ratio of between 1:0.1 to 1:10 of boronophenylalanine (BPA) or any pharmacologically permissible salt, precursor or derivative thereof in water with a saccharide, thereby forming a mixed solution;

increasing the pH of the mixed solution to a pH of about 10, or decreasing the pH of the mixed solution to a pH of about 2; and then, readjusting the pH of the solution to about 7.4, thereby forming a high concentration BPA solution at a physiologically relevant pH.

By "water", I mean water, distilled water, saline solutions and buffered saline solutions, etc.

By "about 10" I mean a pH range of from 8–14. By "about 2" I mean a pH range of from 1–5.

In addition to BPA, structural modifications of BPA or any pharmacologically permissible salt, precursor or derivative thereof, will also work for my invention. These structural modifications include, for example:

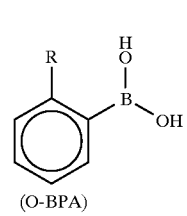

(O-BPA)

(1)

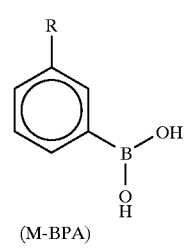

(M-BPA)

(2)

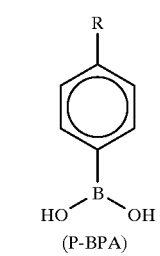

(P-BPA)

(3)

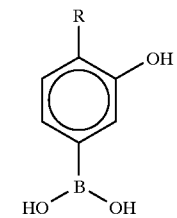

(4)

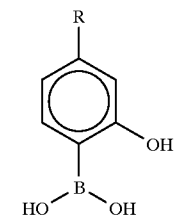

(5)

-continued
(6)
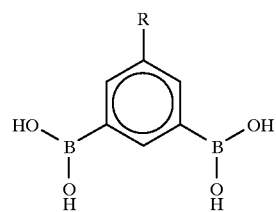
(7)
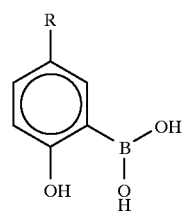
(8)
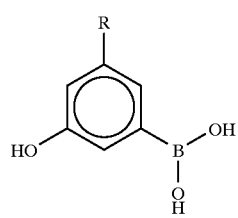
(9)
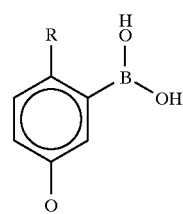
(10)
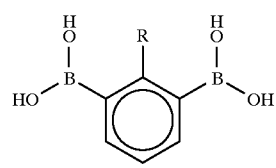
(11)
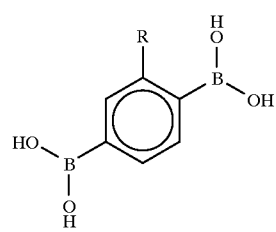
(12)
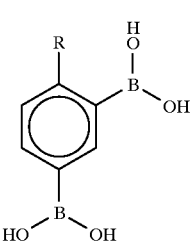
-continued
(13)
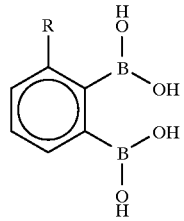
(14)
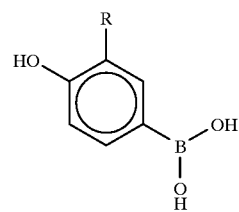
(15)
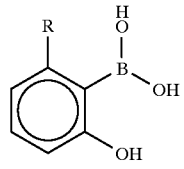
(16)
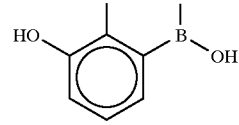
wherein R=
(a)
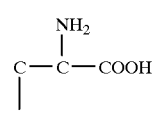
and other structures:
(b)
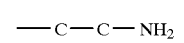
(c)
(d)
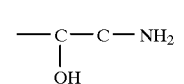
(e)
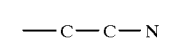
(f)
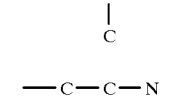
(g)
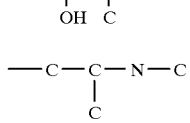

-continued

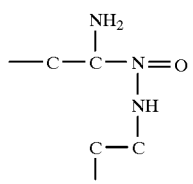
(h)

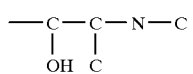
(i)

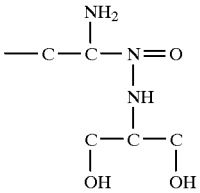
(j)

Also, amino acid analogs of BPA, or any pharmacologically permissible salt, precursor or derivative thereof, will also work for my invention. These amino acid analogs include, for example:

d, I-serine analog:

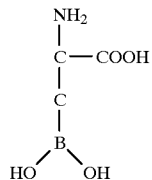

d, I-methionine analog:

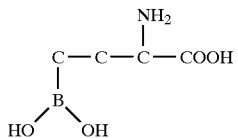

d, I-Asp analog:

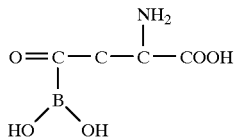

d, I-Glu analog:

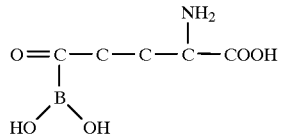

d, I-Thr analog:

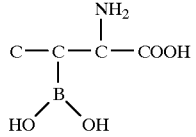

Other objects, advantages, and capabilities of the present invention will become more apparent as the description proceeds.

DETAILED DESCRIPTION OF THE PREFERRED EMBODIMENTS

Figure 1:
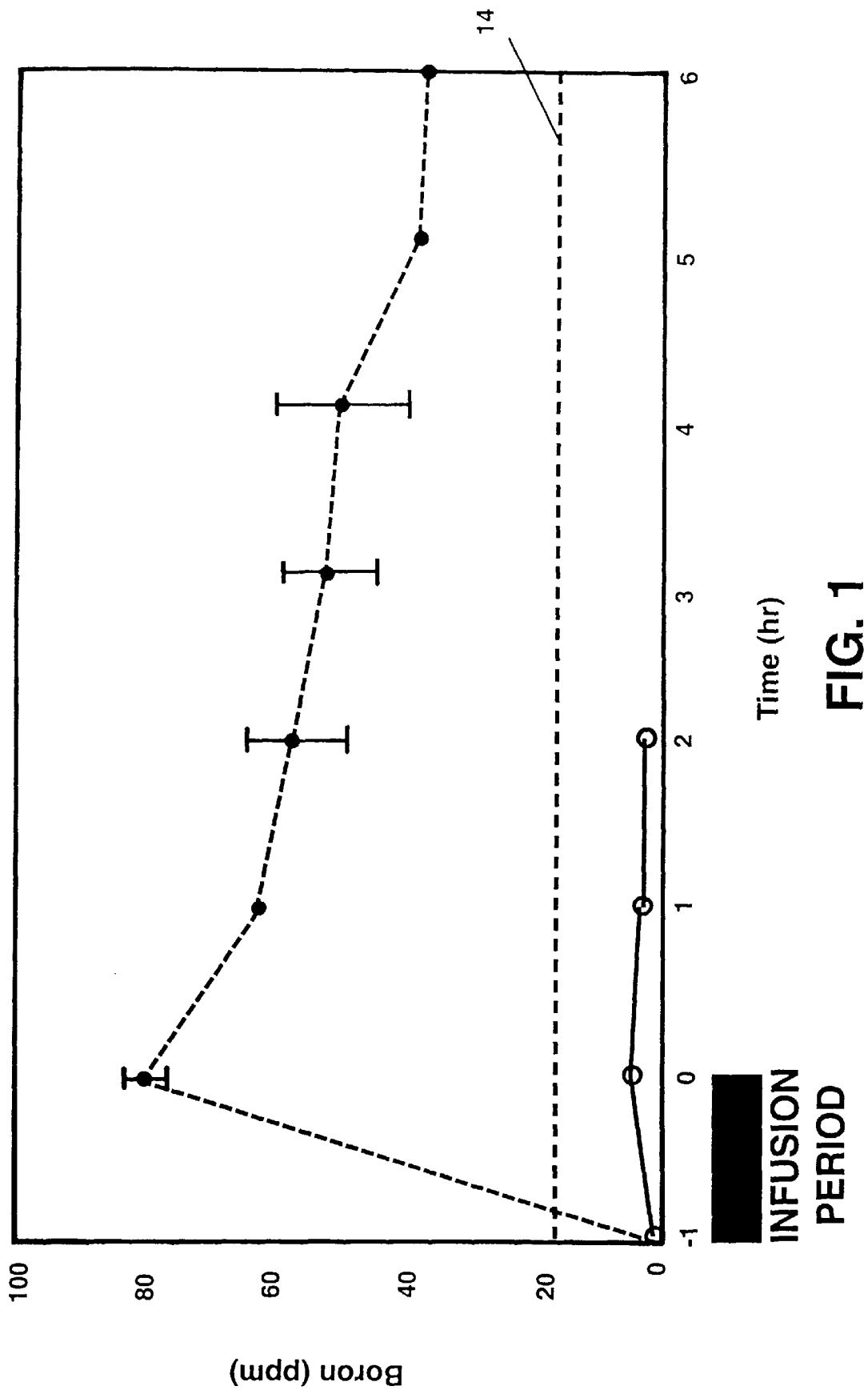
FIG. 1 is a graph of boron concentrations versus time of serum B after infusion of 2,063±55 mg/kg (N=3) of BPA-fructose-water and 99±1.7 mg/kg (N=5) of BPA-buffer formulations into rats; equal volumes of formulation were infused over a one-hour period (−1 to 0 hours).

The novel process as described below creates an injection solution that contains elevated concentrations of boron which enhance the effectiveness of BNCT as a cancer treatment. The process and treatment was performed on rats and mice and can be predicted to be similarly effective in larger animals and humans.

Methods

D- or I-, or I,d- boronophenylalanine and pharmacologically permissible salts thereof can be purchased commercially (e.g., Boron Biologicals, Inc.). For solubility determinations, an excess of BPA was always used. All formulations were sonicated (ultrasonic wave treatment), adjusted to a final pH of 7.4, and filtered through a 0.22 micron filter. The BPA concentration of filtered solutions was calculated from B levels which were measured by inductively coupled plasma atomic emission spectrometry. Formulations used in rat studies were prepared immediately before use; formulations for mouse experiments were prepared within about three days of use. High performance liquid chromatography studies demonstrated that aqueous BPA solutions were stable at physiological (7.4) pH for at least three days. Male Sprague-Dawley rats (300–400 g) and female BD2F1 mice (20–28 g) were anesthetized, a vein cannulated for infusion of the drug, and the femoral artery (rat) cannulated for blood sampling. The drug was infused to rats at target rates of 8.5, 12.8, or 17 ml/kg/hr for 1–3 hours. Mice were infused at target rates of 20 or 1000 mg/kg/min (0.1 or 5.0 ml/kg/min). In rats, urine was collected by bladder cannulation and plasma and serum samples were collected at hourly intervals for 3–7 hours. Each rat received only a single drug formulation. Unless otherwise specified, BPA and B levels are reported as mean±standard error of the mean (SEM) of three experiments. Mice were sacrificed at 1, 2, 4, 6, or 16 hours after infusion of the BPA-fructose-water formulation and tissue collected.

Results

Solubility Studies

B levels in distilled water and in 0.1 M, pH 7.4 phosphate buffer were below the limits of detection (<0.008 mg/ml BPA). The solubility of BPA in the conventional buffer formulation was 2.2±0.4 mg/ml (N=7), but varied slightly as a function of the lot of BPA used. Different BPA lots displayed aqueous solubilities ranging from 1.15 to 3.7 mg/ml. By briefly increasing the pH of the BPA-buffer suspension to about 10 before adjusting it to 7.4, more BPA could be solubilized. Decreasing pH is done by adding an acid, e.g., HCl, and increasing pH by adding a base, e.g., NaOH. A pH 7.4 BPA solution of 6.0±0.1 mg/ml (n=4), prepared by initially increasing pH to about 10, did not precipitate for several hours. However, the greatest increase in solubility was achieved by complexing BPA with monosaccharides and, particularly, with fructose. A 1:1 molar ratio of BPA and fructose mixed together in pH 7.4 distilled water solubilized less than 10 mg/ml BPA. Briefly increasing the pH of a 200 mg/ml BPA-fructose suspension to about 10 and then readjusting pH to 7.4 solubilized 173.2±3.8 mg/ml BPA (N=18, range: 148.6–196.9). The pH adjusted BPA-fructose formulation showed no signs of precipitation over a seven-day observation period and, when added to rat plasma, showed no macroscopic evidence of precipitation. Therefore, with this technique, one may consistently solubilize BPA at a level greater than 33, 50, 75 or even 100 mg/ml.

Rat Studies

Plasma, serum, and tissue samples were collected from rats infused with buffer only, with BPA in buffer (mean BPA concentration: 1.2 mg/ml), with BPA in pH adjusted buffer (mean BPA concentration: 6.0 mg/ml), and with BPA in fructose/water (mean BPA concentration: 173.2 mg/ml). BPA-buffer was infused at a target rate of 17 ml/kg/hr for one hour and actual rates were within 5% of the target value. The BPA-fructose complex was infused at target delivery rates of 12.8 and 17 ml/kg/hr, and delivered BPA doses were 2,217±39 mg/kg (N=15) and 2,917±61 mg/kg (n=8). Actual infusion rates were within 7% of target values. Rats infused at target doses of 12.8 and 17 ml/kg/hr of BPA survived if subject to minimal surgical stress, but rats infused with 4,334±56 mg/kg (target dose: 1,586 mg/kg/hr for 3 hours) all died. Rats infused with BPA doses of 2,148±45 mg/kg (N=6) were sacrificed 6 hours after termination of the BPA infusion, and tissue samples collected for boron analysis.

FIG. 1 illustrates the difference in the time course of serum B when equal volumes of the BPA-fructose complex and the BPA-buffer solution (6 mg/ml) were infused. Serum B values were not significantly different from plasma B levels. If the assumption is made that BPA distributes equally throughout the tissues of the rate (i.e., the rat is viewed as a single, well-stirred compartment), the average tissue distribution of BPA at the termination of the BPA-fructose infusion can be estimated to be 1.58 mg/g, for an average tissue B concentration of 75.7 ppm. Using the same assumption, the average tissue concentration of BPA after infusion of BPA-buffer, can be estimated to be 0.075 mg/g, for an average B concentration of 3.6 ppm. Twenty ppm B is considered the lower limit for effective BNCT as at 14 on FIG. 1. Analysis of tissue samples demonstrated that even six hours after i.v. infusion of target doses of 2,148±45 mg/kg BPA (N=6), tissue B levels greatly exceeded the requirement for effective BNCT (e.g., heart: 42±7 ppm; muscle: 56±10 ppm; lung: 64±19 ppm; liver: 54±14 ppm). Tissue B levels achieved two hours after infusion of the 6 mg/ml BPA-buffer solution were much lower (e.g., heart: 2.3±0.2 ppm; muscle: 3.3±1.6 ppm; lung: 2.7±0.4 ppm; liver: 2.9±0.3 ppm) and tissue levels of B achieved two hours after infusion of 1.2 mg/ml BPA in buffer were lower yet (heart: 1.0 ppm; muscle: 0.8 ppm; lung: 1.1 ppm; liver: 1.0 ppm; N=2). Rats receiving control infusions (no BPA) had tissue B levels near or below the detection limit for B (0.4 ppm). The BPA-fructoe-water solution clearly allows delivery of more B than does the conventional BPA-buffer formulation.

Mouse Studies

In tests on mice carrying malignant melanoma tumors, it was determined that the BPA-fructose complex delivers B to tissues, including tumor tissue. The best treatment schedule identified to date delivered the following tissue B concentrations after intravenous (i.v.) infusion of the pH adjusted BPA-fructose complex:

78.7±16.2 ppm boron to tumor,
20.6±7.3 ppm boron to blood,
22.5±5.2 ppm boron to muscle.

All values are mean±SEM of four animals. Literature reports of boron levels achieved with more standard formulations of BPA generally range around 20 ppm boron delivered to tumor. Since tumor sensitivity to BNCT is increased about 10,000 fold with each doubling of B concentration, the increase from about 20 ppm to 78.7 ppm is very impressive. The increase in tumor B concentration to 78.7 ppm is achieved by the pH adjusting process.

Conclusions

The above studies indicate that pH-adjusted BPA-monosaccharide formulations of BPA increase the delivery of B (BPA) to malignant melanoma cells, while eliciting little or no systemic toxicity. Of the options investigated, BPA complex formulation with fructose appears most promising. Using the fructose formulation, BPA doses of about 3,000 mg/kg could be administered to rats and BPA doses of 2,000–4,000 mg/k could be administered to mice without inducing obvious toxicities. Tissue B levels in rats measured six hours after termination of the infusion were still two-to-four fold greater than the minimum levels (20 ppm deemed necessary for effective BNCT. I.V. infusion of high doses of BPA delivered as a BPA-fructose complex increase the B loading of melanoma cells and so should dramatically facilitate BNCT of malignant melanoma and other cancers.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

I claim:

1. A process for formulating a boronophenylalanine solution for use in a boron neutron capture therapy cancer treatment, the process comprising:
   a. mixing boronophenylalanine (BPA) with a saccharide in water, thereby forming a mixed solution;
   b. increasing the pH of the mixed solution to a pH of about 10; and then,
   c. readjusting the pH of the solution to about 7.4, thereby forming a high concentration BPA solution at a physiologically relevant pH.

2. A process as recited in claim 1 wherein the molar ratio of BPA to the saccharide is between about 10:1 to 1:10.

3. A process as recited in claim 1 wherein the saccharide is fructose.

4. A process for formulating a boronophenylalanine solution for use in a boron neutron capture therapy cancer treatment, the process comprising:
   a. mixing boronophenylalanine (BPA) with a saccharide in water, thereby forming a mixed solution;
   b. decreasing the pH of the mixed solution to a pH of about 2; and then,
   c. readjusting the pH of the solution to about 7.4, thereby forming a high concentration BPA solution at a physiologically relevant pH.

5. A process as recited in claim 4 wherein the molar ratio of BPA to the saccharide is between about 10:1 to 1:10.

6. A process as recited in claim 4 wherein the saccharide is fructose.

7. A product for use in boron neutron capture therapy cancer treatment made by the method comprising:
   a. mixing boronophenylalanine (BPA) with a saccharide in water, thereby forming a mixed solution;
   b. increasing the pH of the mixed solution to a pH of about 10; and then,
   c. readjusting the pH of the solution to about 7.4, thereby forming a high concentration BPA solution of greater than 50 mg/ml at a physiologically relevant pH.

8. A product as recited in claim 7, wherein the molar ratio of BPA to the saccharide is between about 10:1 to 1:10.

9. A product as recited in claim 7, wherein the saccharide is fructose.

10. A product as recited in claim 7, wherein the BPA concentration is greater than 75 mg/ml.

11. A product as recited in claim 7, wherein the BPA concentration is greater than 100 mg/ml.

12. A product for use in boron neutron capture therapy cancer treatment made by the method comprising:
   a. mixing boronophenylalanine (BPA) with a saccharide in water, thereby forming a mixed solution;
   b. decreasing the pH of the mixed solution to a pH of about 2; and then,
   c. readjusting the pH of the solution to about 7.4, thereby forming a high concentration BPA solution of greater than 50 mg/ml at a physiologically relevant pH.

13. A product as recited in claim 12, wherein the molar ratio of BPA to the saccharide is between about 10:1 to 1:10.

14. A product as recited in claim 12, wherein the saccharide is fructose.

15. A product as recited in claim 12, wherein the BPA concentration is greater than 75 mg/ml.

16. A product as recited in claim 12, wherein the BPA concentration is greater than 100 mg/ml.

17. An aqueous solution for use in a boron neutron capture therapy cancer treatment comprising, in a concentration of greater than 50 mg/ml, a compound selected from the group consisting of boronphenylalanine (BPA), a structural modification of BPA, or an amino acid analog of BPA.

18. A solution as recited in claim 17, wherein the BPA concentration is greater than 75 mg/ml.

19. A solution as recited in claim 17, wherein the BPA concentration is greater than 100 mg/ml.

* * * * *